(12) United States Patent
Wiseman, Sr. et al.

(10) Patent No.: US 6,379,242 B1
(45) Date of Patent: Apr. 30, 2002

(54) AUTOMATIC SCENT DISPENSING SYSTEM

(76) Inventors: Larry E. Wiseman, Sr., 400 N. Star St., Jackson, OH (US) 45640; Rodney D. Goheen, R.R. Box 408, Cynthiana, KY (US) 41031

( * ) Notice: Subject to any disclaimer, the term of this patent is extended or adjusted under 35 U.S.C. 154(b) by 0 days.

(21) Appl. No.: 09/759,071

(22) Filed: Jan. 12, 2001

(51) Int. Cl.[7] .................................................. F24F 3/16
(52) U.S. Cl. ........................ 454/337; 422/124; 222/647
(58) Field of Search ........................... 454/75, 110, 157, 454/256, 328, 337; 422/123, 124; 261/DIG. 17; 222/644, 645, 646, 647, 648

(56) References Cited

U.S. PATENT DOCUMENTS

| | | | |
|---|---|---|---|
| 2,497,068 A | | 2/1950 | Canney |
| 2,558,329 A | * | 6/1951 | Abbott |
| 3,499,579 A | | 3/1970 | Garratt |
| 4,159,672 A | * | 7/1979 | Garguilo et al. ............ 454/337 |
| 4,601,886 A | | 7/1986 | Hudgins |
| 4,903,583 A | * | 2/1990 | Frazier |
| D314,237 S | | 1/1991 | Blumantahl, Jr. |
| 5,297,988 A | * | 3/1994 | Nishino et al. ............... 454/75 |
| 5,788,569 A | | 8/1998 | Lee |

* cited by examiner

Primary Examiner—Harold Joyce

(57) ABSTRACT

A automatic scent dispensing system for distributing scents throughout a building on a user-adjustable schedule without requiring user attention. The automatic scent dispensing system includes a tank system for holding a scent substance, with the tank system including a tank housing having a plurality of reservoirs for holding a scent substance therein. A selector valve selects flow from one of the reservoirs. A pump pumps the scent substance out of the reservoirs. A dispensing nozzle mounts on the duct of the air circulating system such that an orifice of the nozzle is in communication with the air passage of the duct. The dispensing nozzle is connected to and in fluid communication with the outlet of the pump. A duration timer selectively controls a duration of dispensing of the scent substance. The duration timer controls supply of electrical power to the pump, and is adjustable to set the duration of the supply of electrical power to the pump for dispensing the scent substance. The duration timer is triggered to supply electrical power to the pump for the selected time duration by a trigger. An occurrence timer selectively controls a time period between occurrences of dispensing of the scent substance. The occurrence timer triggers the duration timer after passage of a selected time period. A regular/irregular selector switch controls the actuation of the duration timer. The selector switch has an irregular setting wherein the trigger is sent to the duration timer by the fan switch of the air circulating system upon operation of the fan of the air circulating system. The selector switch also has a regular setting wherein the trigger is sent to the duration timer by the occurrence timer upon the passage of the selected time period.

10 Claims, 4 Drawing Sheets

AUTOMATIC SCENT DISPENSING SYSTEM

BACKGROUND OF THE INVENTION

1. Field of the Invention

The present invention relates to whole building air scenting systems and more particularly pertains to a new automatic scent dispensing system for distributing scents throughout a building on a user-adjustable schedule without requiring user attention.

2. Description of the Prior Art

The use of whole building air scenting systems is known in the prior art. While some of these systems perform some operations without user intervention or attention, most, if not all, of the known systems require some type of periodic attention by the user for the system to operate, such requiring the user to initiate the operation of the system. Thus, these systems cannot be set and relied upon to operate without the user's periodic attention or monitoring. This may result in the accumulation of odors or smells in the building to an offensive level, which may be the only reminder that the user is given that the system has not been operated frequently enough.

The automatic scent dispensing system according to the present invention substantially departs from the conventional concepts and designs of the prior art, and in so doing provides an apparatus primarily developed for the purpose of distributing scents throughout a building on a user-adjustable schedule without requiring user attention.

SUMMARY OF THE INVENTION

In view of the foregoing disadvantages inherent in the known types of whole building air scenting systems now present in the prior art, the present invention provides a new automatic scent dispensing system construction wherein the same can be utilized for distributing scents throughout a building on a user-adjustable schedule without requiring user attention.

To attain this, the present invention generally comprises a tank system for holding a scent substance, with the tank system including a tank housing having a plurality of reservoirs for holding a scent substance therein. A selector valve selects flow from one of the reservoirs. A pump pumps the scent substance out of the reservoirs. A connection conduit fluidly connects an output of the selector valve and the inlet of the pump. An outlet conduit is in communication with the outlet of the pump for receiving the scent substance pumped by the pump. A dispensing nozzle mounts on the duct of the air circulating system such that an orifice of the nozzle is in communication with the air passage of the duct. The dispensing nozzle is connected to and is in fluid communication with the outlet of the pump through the outlet conduit. A duration timer selectively controls a duration of dispensing of the scent substance. The duration timer controls supply of electrical power to the pump, and is adjustable to set the duration of the supply of electrical power to the pump for dispensing the scent substance. The duration timer is triggered to supply electrical power to the pump for the selected time duration by a trigger. An occurrence timer selectively controls a time period between occurrences of dispensing of the scent substance. The occurrence timer triggers the duration timer after passage of a selected time period. A regular/irregular selector switch controls the actuation of the duration timer. The regular/irregular selector switch has an irregular setting wherein the trigger is sent to the duration timer by the fan switch of the air circulating system upon operation of the fan of the air circulating system. The regular/irregular selector switch also has a regular setting wherein the trigger is sent to the duration timer by the occurrence timer upon the passage of the selected time period.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
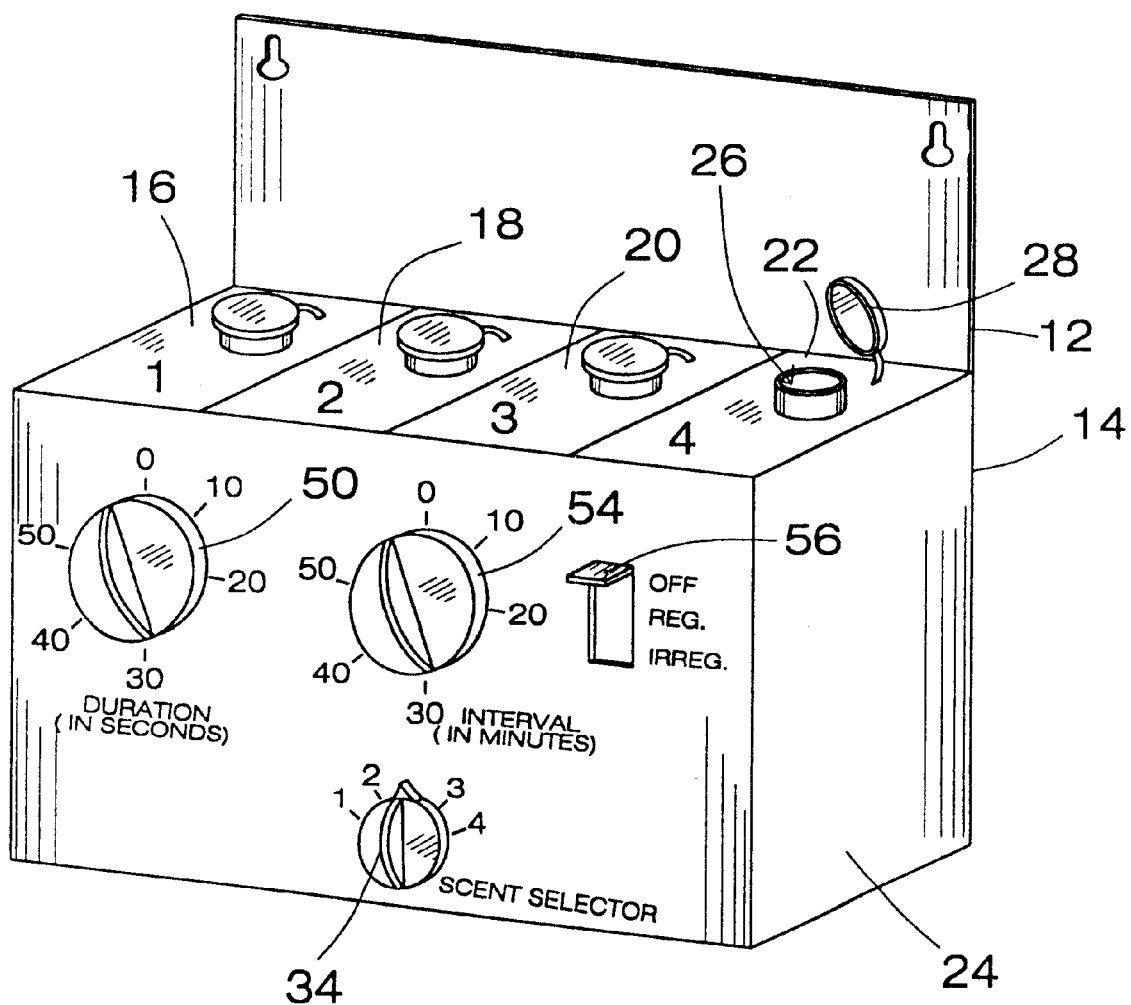
FIG. 1 is a schematic perspective view of a new automatic scent dispensing system according to the present invention.
Figure 2:
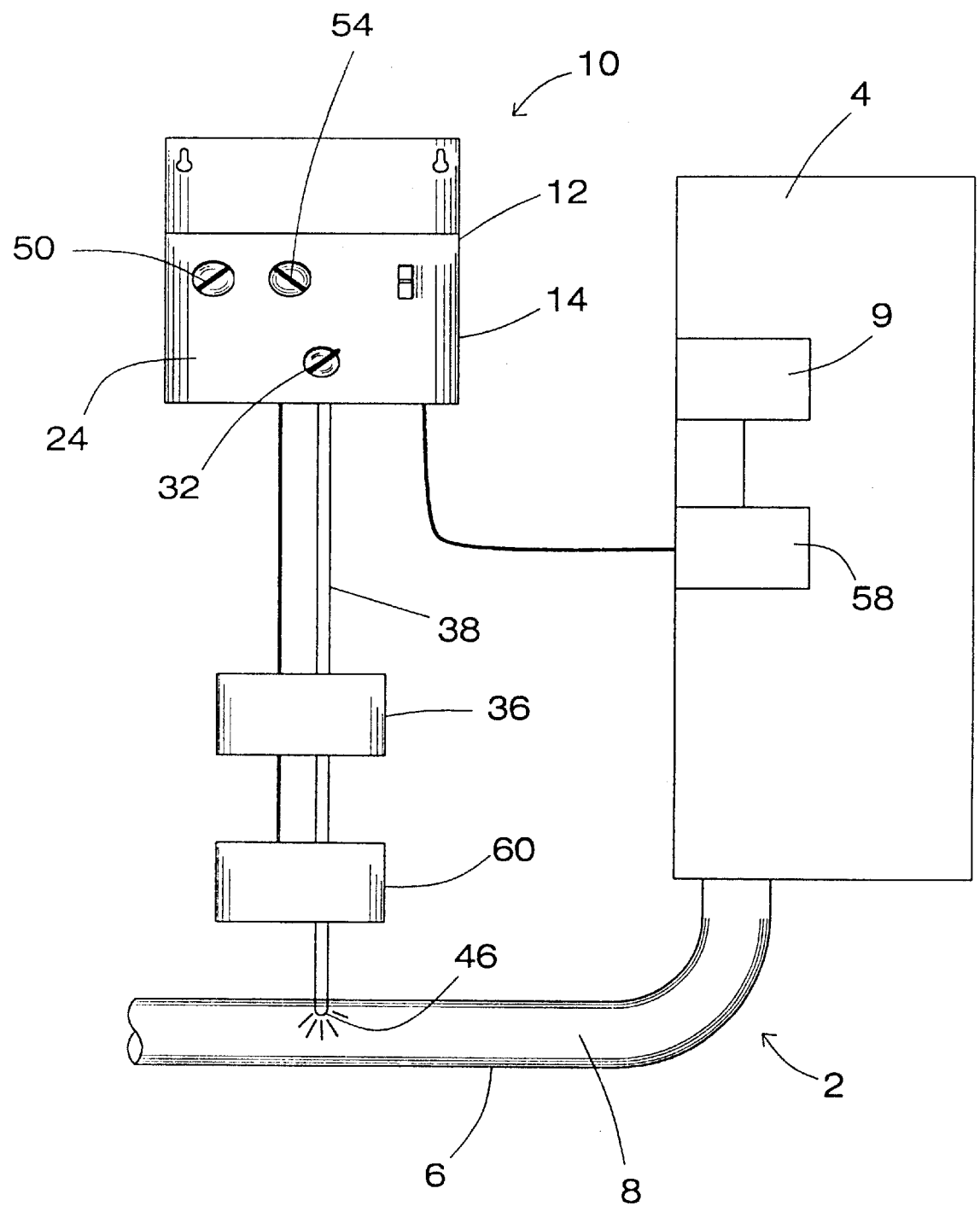
FIG. 2 is a schematic diagram of the present invention in relation to an air circulating system.
Figure 3:
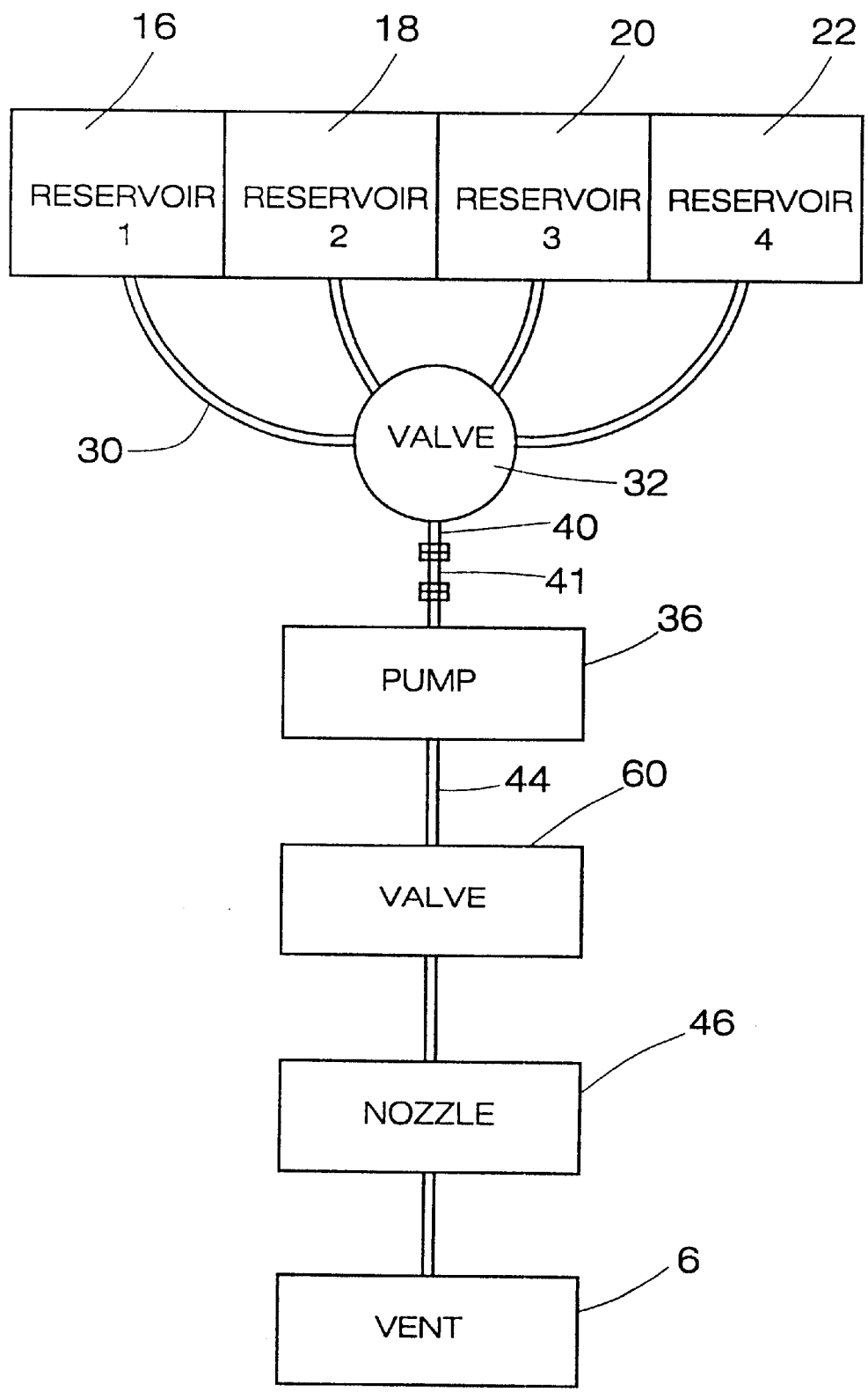
FIG. 3 is a schematic diagram of scent substance movement in the present invention.
Figure 4:
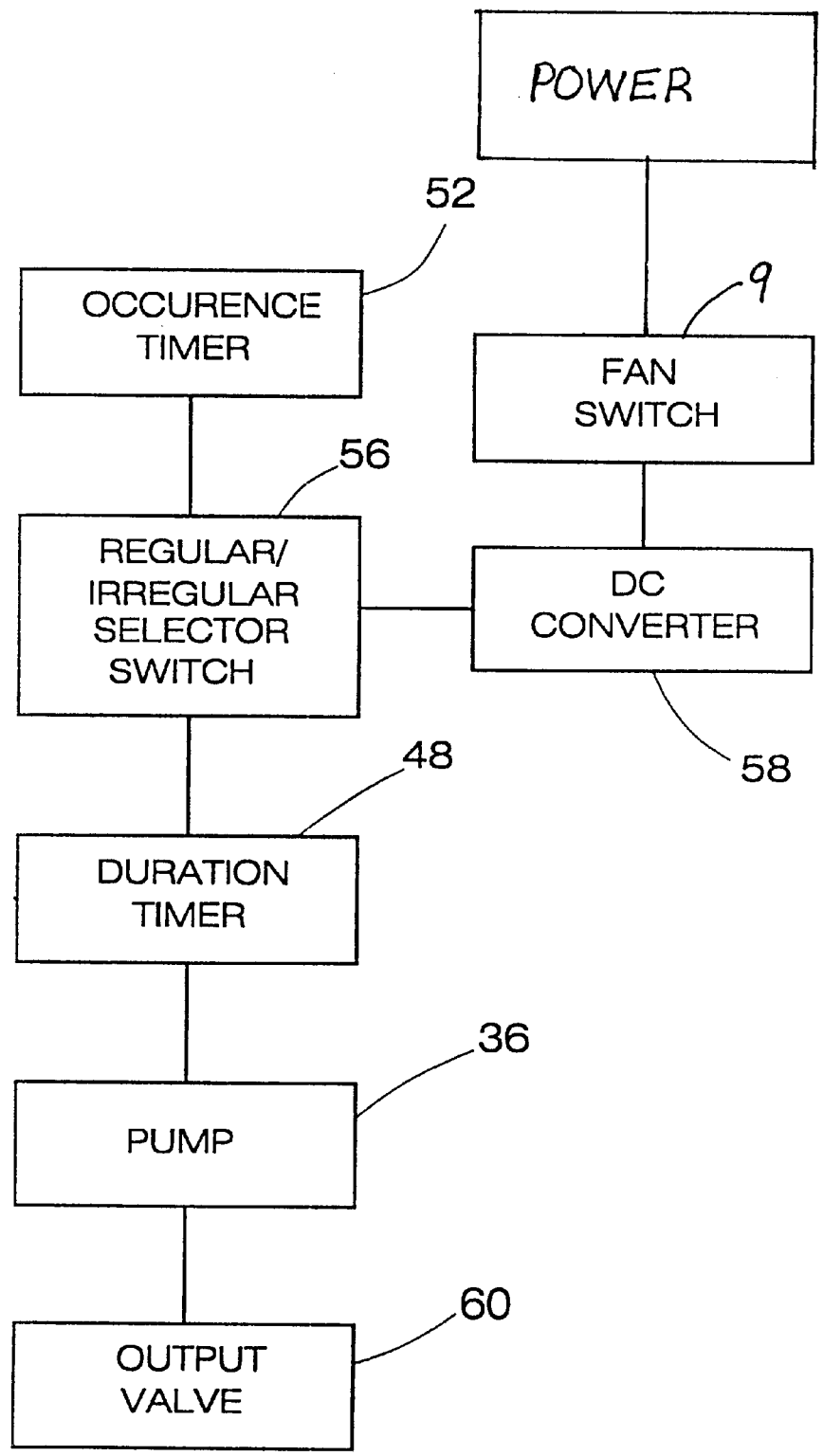
FIG. 4 is a schematic diagram of operational control in the present invention.

With reference now to the drawings, and in particular to FIGS. 1 through 4 thereof, a new automatic scent dispensing system embodying the principles and concepts of the present invention and generally designated by the reference numeral 10 will be described.

The scent distribution system 10 of the invention is highly suitable for use with an air circulating system 2 for a building, such as, for example, a heating system including a furnace 4 or a cooling system including an air conditioner.

The air circulating system typically has at least one duct 6 associated with it, and the duct has an air passage 8 through which air is passed prior to introduction of the air into the living space of the building. The air circulating system also typically has a fan for moving air through the air circulating system and a fan switch 9 for selectively supplying electrical power to the fan to operate the fan and move air through the air passage of the duct.

The scent distribution system 10 of the invention includes a tank system 12 for holding a scent substance for dispensing into the duct of the air circulating system. The tank system includes a tank housing 14 that has an interior. A reservoir 16 is formed in the interior of the tank housing for holding the scent substance, which typically is in liquid form, and the reservoir is adapted for holding the liquid scent substance. Preferably, at least two reservoirs are formed in the interior of the tank housing for holding two scent substances separate from each other. In the exemplary embodiment of the invention, the interior of the tank housing forms four reservoirs 16, 18, 20, 22, a feature which is convenient for holding a different scent for each of the seasons of the year. Illustratively, each of the reservoirs holds approximately one pint of the scent substance that permits dispensing of the scent substance for an extended period without requiring refilling of the reservoir. The tank housing has an exterior surface 24, and the exterior surface may formed into the appearance of a common household item, such as, for example, a flower pot or a candle arrangement. A mounting tab may be formed on the tank housing for receiving a fastener for mounting the tank housing to a vertical wall surface.

Each of the reservoirs of the tank housing preferably has a top opening 26 for filling the reservoir with the liquid scent substance. A lid 28 may be mounted on the tank housing for closing the top opening of the reservoir. A feed conduit 30 is provided in the tank housing and is in fluid communication with the reservoir, with each of the reservoirs having a feed conduit associated with it. Each feed conduit has an inlet into a lower portion of the associated reservoir. A selector valve 32 is provided for selecting flow from one of the reservoirs for dispensing into the air circulating system. The selector valve is in communication with each of the feed conduit of the reservoirs. The selector valve preferably has a valve handle 34 that is rotatable between a position for selecting flow from each of the reservoirs, and the selector valve has an output through which flows the scent substance of the selected reservoir.

A pump 36 may be provided for pumping the scent substance out of the reservoir, especially if the scent substance is in liquid form. The pump has an inlet that is in fluid communication with the output of the selector valve of the tank housing. The pump also has an outlet through which the selected scent substance is pumped under pressure. The pump may be mounted on the tank housing, or may be mounted a distance from the housing. A connection conduit 38 may be provided for fluidly connecting the output of the selector valve and the inlet of the pump for permitting remote mounting of the pump from the tank housing. The connection conduit has a length that may be comprised of a plurality of segments 40, 41 that are removably connected together so that one or more segments may be removed from (or added to) the length of the connection conduit for decreasing (or increasing) the length of the connection conduit, and thereby adjusting the distance between the pump and the tank housing.

An outlet conduit 44 is provided that is in fluid communication with the outlet of the pump for receiving the scent substance pumped by the pump. A dispensing nozzle 46 is provided for dispensing the scent substance into the air flow through the air passage in the duct of the air circulating system, and the nozzle may be mounted on a wall of the duct 6 such that an orifice of the nozzle is in communication with the air passage. The dispensing nozzle is connected to and is in fluid communication with the outlet of the pump by means of the outlet conduit. Preferably, the orifice of the dispensing nozzle being adapted to produce a fine mist of the scent substance.

One significant feature of the invention which reduces the attention that a user must pay to the scent distribution system is a duration timer 48 which is provided for selectively controlling a duration of scent substance dispensing into the air circulating system. The duration timer controls the supply of electrical power to the pump, starting the flow of electrical power to the pump when dispensing of the scent substance is desired and stopping the flow of electrical power to the pump when dispensing is desired to be stopped. The duration timer is adjustable to permit the user to set the duration of the supply of electrical power to the pump, thus setting the duration of the dispensing of the scent substance by the nozzle into the air circulating system. In an exemplary embodiment of the invention, the duration timer is adjustable for time durations ranging between and including one second and 60 seconds. The duration timer preferably has a duration selector 50 for adjusting the time duration setting of the duration timer. The duration selector may be adapted to visually indicate a time duration setting of the duration timer, such as a knob with markings alignable with markings on a base surface which indicate various time durations. The duration timer may be mounted on the tank housing, with electrical power supply wires extending with the connection conduit to the pump.

Another significant feature of the invention, one which further minimizes the attention that a user must give to the operation of the system, is an occurrence timer 52 which is provided for selectively controlling the time period between occurrences of dispensing of the scent substance. The occurrence timer may trigger operation of the duration timer after the passage of a selected time period since the previous time that the duration timer was triggered. Preferably, the occurrence timer is adjustable to set a length of the time period between triggerings of the duration timer, and thus between dispensings of the scent substance. An occurrence selector 54 may be provided for making this adjustment. In the exemplary embodiment of the invention, the occurrence timer is adjustable for time periods between one minute and 60 minutes, although the provision for longer time periods is possible.

The duration timer is triggered to supply electrical power (at any desired voltage) to the pump for the selected time duration by a trigger, which may comprise the supply of electrical power to the duration timer so that the duration timer can supply electrical power to the pump for the selected duration. To control what triggers the actuation of the duration timer, an regular/irregular selector switch 56 is preferably provided. The regular/irregular selector switch may have an irregular setting wherein the trigger is sent to the duration timer by the fan switch of the air circulating system upon operation of the fan of the air circulating system. In this mode, the duration timer is triggered every time that the fan of the air circulation system begins operation. (The circuitry necessary for providing one trigger per fan cycle is conventionally known, and not described herein.) The occurrence timer does not control the time periods between scent dispensings, which is strictly a function of the cycling of the fan by, for example, a thermostat associated with the air circulating system. In the case where the fan switch operates on household alternating current, such as approximately 110 volts, a DC converter 58 may be employed to step down the voltage and convert the alternating current to direct current. In one preferred embodiment of the invention, power for the system of the invention is supplied through the fan switch (and the DC converter, if needed).

The regular/irregular selector switch may have a regular setting wherein the trigger is sent to the duration timer by the occurrence timer upon the passage of the selected time period. In this mode, the duration timer is triggered every time the time period set on the occurrence selector passes. Optionally, the occurrence timer may trigger the duration timer, and the duration timer circuitry may wait until the next time the fan is actuated by the system (e.g., the thermostat) to provide electrical power to the pump.

Optionally, a output valve 60 may be provided in the output conduit from the pump for opening when the pump is provided with electrical power and closing when power is withdrawn from the pump. Such output valve may be actuated by a solenoid that is activated by the provision of electrical power to remove a blockage from the output conduit.

In use, the user fills the reservoirs with the desired scent substances and sets the valve handle to the reservoir to the reservoir having the scent that is to be currently dispensed. The user sets the duration selector to the desired time of dispensing of the scent. To achieve a higher level of the scent in the air in the building, the duration selector is set to a longer duration, and for a lower level of scent in the air the duration selector is set to a shorter duration. The regular/irregular selector switch is set to the desired position, and if the selector is set to regular, the duration selector is set to the desired time period between dispensings of the scent.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A scent distribution system for an air circulating system for a building, the air circulating system having a duct with an air passage through which air is passed prior to introduction of the air into the living space of the building, the air circulating system having a fan for moving air through the air circulating system, the air circulating system having a fan switch for selectively supplying electrical power to the fan, the system comprising:

tank system for holding a scent substance, the tank system including a tank housing having a plurality of reservoirs for holding a scent substance therein, and a selector valve for selecting flow from one of the reservoirs;

a pump for pumping the scent substance out of the reservoirs, the pump having an inlet and an outlet;

a connection conduit for fluidly connecting an output of the selector valve and the inlet of the pump;

an outlet conduit in communication with the outlet of the pump for receiving the scent substance pumped by the pump;

a dispensing nozzle for mounting on the duct of the air circulating system such that an orifice of the nozzle is in communication with the air passage of the duct, the dispensing nozzle being connected to and in fluid communication with the outlet of the pump through the outlet conduit;

a duration timer for selectively controlling a duration of dispensing of the scent substance, the duration timer controlling supply of electrical power to the pump, the duration timer being adjustable to set the duration of the supply of electrical power to the pump for dispensing the scent substance, the duration timer being triggered to supply electrical power to the pump for the selected time duration by a trigger;

an occurrence timer for selectively controlling a time period between occurrences of dispensing of the scent substance, the occurrence timer triggering the duration timer after passage of a selected time period;

a regular/irregular selector switch for controlling the actuation of the duration timer, the regular/irregular selector switch having an irregular setting wherein the trigger is sent to the duration timer by the fan switch of the air circulating system upon operation of the fan of the air circulating system, the regular/irregular selector switch having a regular setting wherein the trigger is sent to the duration timer by the occurrence timer upon the passage of the selected time period.

2. The scent distribution system of claim 1 wherein the duration timer being adjustable for time durations between one second and 60 seconds, the duration timer having a duration selector for adjusting the time duration, the duration selector being adapted to visually indicate a time duration setting of the duration timer, the duration timer being mounted on the tank housing.

3. The scent distribution system of claim 1 wherein the occurrence timer is adjustable to set a length of the time period.

4. The scent distribution system of claim 3 wherein the occurrence timer is adjustable for time periods between one minute and 60 minutes.

5. The scent distribution system of claim 1 wherein the interior of the tank housing forms four reservoirs.

6. The scent distribution system of claim 1 wherein the selector valve has a valve handle rotatable between a position for selecting flow from each of the reservoirs.

7. The scent distribution system of claim 1 wherein a mounting tab is formed on the tank housing for receiving a fastener for mounting the tank housing to a vertical wall surface.

8. The scent distribution system of claim 1 wherein the connection conduit has a length comprised of a plurality of segments removably connected together such that segments may be removed from the length of the connection conduit for decreasing the length of the connection conduit.

9. The scent distribution system of claim 1 wherein the orifice of the dispensing nozzle is adapted to produce a fine mist of the scent substance.

10. The scent distribution system of claim 1 wherein each of the reservoirs has a top opening for filling the reservoir with scent substance, and including a lid mounted on the tank housing for closing the top opening of each of the reservoirs.

\* \* \* \* \*